(12) United States Patent
Guerret et al.

(10) Patent No.: US 10,271,547 B2
(45) Date of Patent: Apr. 30, 2019

(54) PARTICLES CONTAINING PHEROMONES AND PRODUCTION PROCESS

(71) Applicant: MELCHIOR MATERIAL AND LIFE SCIENCE FRANCE, Lacq (FR)

(72) Inventors: Olivier Guerret, Pern (FR); Samuel Dufour, Orthez (FR)

(73) Assignee: MELCHIOR MATERIAL AND LIFE SCIENCE FRANCE, Lacq (FR)

( * ) Notice: Subject to any disclaimer, the term of this patent is extended or adjusted under 35 U.S.C. 154(b) by 0 days.

(21) Appl. No.: 15/551,723

(22) PCT Filed: Feb. 17, 2016

(86) PCT No.: PCT/EP2016/053385
§ 371 (c)(1),
(2) Date: Aug. 17, 2017

(87) PCT Pub. No.: WO2016/131883
PCT Pub. Date: Aug. 25, 2016

(65) Prior Publication Data
US 2018/0064102 A1     Mar. 8, 2018

(30) Foreign Application Priority Data

Feb. 18, 2015 (FR) ...................................... 15 51374

(51) Int. Cl.
*A01N 25/28* (2006.01)
*A01M 1/02* (2006.01)
(Continued)

(52) U.S. Cl.
CPC ............. *A01N 25/28* (2013.01); *A01M 1/023* (2013.01); *A01M 7/00* (2013.01); *A01N 25/04* (2013.01); *A01N 63/02* (2013.01); *A01M 1/10* (2013.01)

(58) Field of Classification Search
CPC ................................ A01N 25/28; A01N 63/02
See application file for complete search history.

(56) References Cited

U.S. PATENT DOCUMENTS 6,090,077 A * 7/2000 Shaw .................. A61M 5/3234
604/110
6,171,286 B1 * 1/2001 Gross .................... A61M 5/315
604/218

(Continued)

FOREIGN PATENT DOCUMENTS

WO     WO 99/56541 A1    11/1999
WO     WO 00/48465 A1     8/2000
(Continued)

OTHER PUBLICATIONS

International Search Report (PCT/ISA/210) issued in PCT/EP2016/053385, dated Mar. 29, 2016.
(Continued)

*Primary Examiner* — Carlos A Azpuru
(74) *Attorney, Agent, or Firm* — Birch, Stewart, Kolasch & Birch, LLP (57) ABSTRACT

The present invention is directed towards microparticles consisting of a solid shell made of polymer, in particular an acrylic polymer, surrounding a core comprising a mixture of oil and wax and also pheromone. The present invention is also directed towards a production process and the use of an aqueous suspension of such microparticles containing pheromones comprising fatty chains, such as lepidopteran pheromones, and which are capable of releasing the pheromones in a sustained manner.

12 Claims, 2 Drawing Sheets

(51) Int. Cl.
*A01M 7/00* (2006.01)
*A01N 25/04* (2006.01)
*A01N 63/02* (2006.01)
*A01M 1/10* (2006.01)

(56) References Cited

U.S. PATENT DOCUMENTS

2010/0203170 A1 8/2010 Guerret et al.
2014/0178485 A1 6/2014 Champagne et al.

FOREIGN PATENT DOCUMENTS

| WO | WO 2009/007810 A1 | | 1/2009 |
| WO | WO 2012/095444 A2 | | 7/2012 |
| WO | 2012130823 A1 | * | 10/2012 |
| WO | WO 2014/096622 A1 | | 6/2014 |

OTHER PUBLICATIONS

Written Opinion (PCT/ISA/237) issued in PCT/EP2016/053385, dated Mar. 29, 2016.

Atterholt et al., "Controlled release of insect sex pheromones from paraffin wax and emulsions," Journal of Controlled Release, vol. 57, 1999, pp. 233-247.

Bartell Csiro, "Mechanisms of communication disruption by pheromone in the control of Lepidoptera: a review," Physiological Entomology, vol. 7, No. 4, 1982, pp. 353-364.

Cardé, "Principles of mating disruption," Behavior-Modifying Chemicals for Pest Management: Applications of Pheromones and Other Attractants, 1990, pp. 47-71.

De Vlieger, "Development of a sprayable slow-release formulation for the sex pheromone of the Mediterranean corn borer, *Sesamia nonagroides*," Environmentalisht, vol. 28, 2008 (Published online Jul. 6, 2007), pp. 45-48.

French Preliminary Search Report for Application No. 1551374, dated Sep. 15, 2015.

Gu et al., "Comparisons of simple complex coacervations for preparation of sprayable insect sex pheromone microcapsules and release control of the encapsulated pheromone molecule," Journal of Microencapsulation, vol. 27, No. 4, 2010, pp. 355-364.

Kong et al., "Spreadable dispersion of insect sex pheromone capsules, preparation via complex coacervation and release control of the encapsulated pheromone component molecule," Biomedical Microdevices, vol. 11, 2009 (Published online Sep. 27, 2008), pp. 275-285.

* cited by examiner

FIGURE 3

PARTICLES CONTAINING PHEROMONES AND PRODUCTION PROCESS

The present invention relates to the production and use of weakly-charged microparticles that contain fatty-chain pheromones, such as lepidopteran pheromones, and that are capable of releasing the pheromones in a sustained manner. These microparticles also have the distinctive feature of being more than 97% by weight composed of natural, biodegradable products manufactured by an environmentally-friendly process.

PRIOR ART

The use of pheromones to control insect crop pest populations is well-known to a person skilled in the art. Since insect invasions occur several times each season, it is necessary to solve the problem of diffusing, throughout the season, a sufficient amount of pheromone to either guide the insects toward an insect trap or to saturate the insects' antennas, which normally enable a male to find females (or vice-versa): see Behavior-modifying chemicals for insect management: applications of pheromones and other attractants (Chapter 4 edited by Richard L. Ridgway, Robert M. Silverstein, May N. Inscoe) or Mechanisms of communication disruption by pheromone in the control of Lepidoptera: a review (1982; Physiological Entomology Volume 7, Issue 4, pages 353-364).

Various diffusion techniques exist. Mention may be made, for example, of wick bottles such as those sold under the Rhyncotrak™ or Rhyncopr™ brands, plastics (Cosmotrack™) or gels soaked with the pheromone-containing substance (for example US 20110014257, or U.S. Pat. No. 8,828,374 B2), porous plastic capsules (BASF products for example sold under the Rak brand) or programmable vaporizer technologies (US 2008/0184614, or Checkmate™ brand). These techniques, as interesting as they are, have many defects, such as their cost of implementation (which includes the installation and removal of diffusers) and their cost of production. Furthermore, the stability of some of these systems over the crop treatment period is also a limiting factor.

The consequences of these defects are important since they are a burden on the development of pheromone-based crop treatment technology: even if the ecological balance of a pheromone-based treatment is very good, having too high a price compared to conventional phytosanitary products or being too difficult to apply for a given crop prevents adoption of the pheromone crop-treatment solution.

A solution for improving the practicability and the efficacy of pheromone-release systems consists in encapsulating these pheromones (or the pheromonal mixture) in more or less fine particles that can then be dispersed in a carrier solvent (generally water). Prior work has described pheromone encapsulation technologies.

These technologies can be classified in broad categories:
1) Coacervation Technologies:
According to this principle, the pheromone is solubilized in solvent and this mixture is emulsified to obtain droplets. A recent example of this kind in technology will be found in the article by Gu et al. (Journal of Microencapsulation, 2010, 27 (4), 355-364) or X. Zheng et al. (Biomed Microdevices (2009), 11, p. 275). Coacervation is classified as simple coacervation or complex coacervation depending on whether it involves one or two oppositely-charged polymers.

Simple coacervation occurs in four steps, consisting first in preparing a 1% or 5% solution of water-soluble polymer in water, then in emulsifying the pheromone in this solution in the presence of surfactants. In a third step, addition of a salt such as sodium sulfate under rapid stirring enables the flocculation of the polymers around the droplets and, finally, the cross-linking of a shell by adding formaldehyde or glutaraldehyde.

Complex coacervation, in turn, consists in first preparing an aqueous cationic polymer solution in which the pheromone is emulsified and then, separately, preparing an anionic polymer solution at the same concentration as before. Lastly, the emulsion and the solution are simultaneously pumped into a stirred reactor to create a suspension of particles having a double polymer shell (anionic on the outside and cationic on the inner layer). Lastly, to improve the particles' stability, formaldehyde cross-linking is carried out.

In both cases, the particle suspensions must be washed several times to remove non-encapsulated pheromone. That illustrates a first limitation of these technologies, which do not have 100% encapsulation yield, but it is essential that all the pheromone is encapsulated to limit application costs. In this system, the particles are thus hollow and when used in the field, the pheromone is designed to be constantly diffused through a thin porous membrane for several weeks. It is observed that that is difficult to control by this technology, in particular because a substantial portion of the pheromone is adsorbed on the surface of the particles and is released immediately. The best results involve large amounts of formaldehyde or glutaraldehyde, which are highly toxic compounds that pose potential pollution problems when this technology is applied to food crops.

2) Polymer Capsule Technologies
These technologies are illustrated by J. de Viegler (Environmentalist 2008 p. 45) and they consist first in dissolving a polymer in an organic solvent that is more volatile than water, such as dichloromethane, and adding the pheromone thereto. The solution obtained is then emulsified in water and then the solvent is evaporated. The suspension obtained is then dried to obtain a powder capable of releasing pheromones for 25 days. The difficulty of this technology consists in the fact that the volatile solvent is harmful to the environment and to users and that, furthermore, traces of this solvent can have a negative effect on the attractive power of the pheromones.

3) Cryogenic Grinding Technologies
These technologies consist in grinding a plastic material soaked with pheromone obtained beforehand either by polymerization in the presence of pheromone or by soaking said plastic in a bath containing pheromone solution in a suitable organic solvent. To obtain a powder of pheromone-releasing particles, the material should then be subjected to low-temperature grinding. This technology is expensive.

4) Technologies for Emulsifying an Organic Formulation Containing the Pheromone
These technologies are illustrated for example in the patent US 2007/0071786 (for film applications) or the publication by C. A. Atterholt et al. (Journal of Controlled Release, 57 (1999), 223) or the patent U.S. Pat. No. 6,001, 346A (for vaporizer applications). They consist in selecting a wax having a melting point below 100° C., and preparing a molten mixture of pheromone and wax above this melting point but below 100° C. Furthermore, it is necessary to prepare an aqueous surfactant solution into which the organic solution is cast under rapid stirring. The surfactants used are sorbyl laurate (Span 60) or triethanolamine stearate, microcrystalline cellulose or carrageenan gum. Only triethanolamine stearate is used for the vaporizable applications;

the other surfactants are used for film applications. The advantage of these technologies is to show highly-controlled diffusion rates while using a natural carrier (wax).

The limitation of this technology lies in the fact that emulsification requires strong agitation requiring Ultra Turrax-type dispersing devices. Furthermore, the emulsions thus obtained are metastable mixtures and the paraffin/water mixture ends up settling out after a few days or a few months, which makes industrial exploitation of these solutions difficult.

Furthermore, encapsulation technologies have also been described in fields other than pheromones. The document WO 2008/146119 (Coatex) describes the use of HASE-type emulsions to trap fragrance molecules by adjusting the pH of the mixture.

Also, the document WO 2014/96622 (Coatex) describes the use of an HASE-type acrylic copolymer and at least one solid-liquid phase change material having a phase transition temperature ranging from 20° C. to 90° C. for preparing polymeric microcapsules of an active agent, the presence of a phase change material improving the mechanical strength of the microcapsules. Although being suitable for a certain number of fields of application, the microparticles obtained according to the formulas described in this last document have in certain other applications the disadvantage of being too hard, of cracking or of lacking flexibility. That is notably the case when the microparticles must grip the surfaces on which they are deposited, for example a fabric or a rough surface. In addition, the process for encapsulating active ingredients according to WO2014/96622 is directed to active ingredients that must remain inside the capsules and not diffuse. The release of the active ingredient is achieved by modification of the pH, the temperature or by mechanical alteration of the shell. It is necessary modify or alter the shell so that the active ingredient is released and this release is not done passively and gradually without external intervention.

The document WO2012095444 describes an encapsulation process via free-radical polymerization which polymerizes an acrylate dissolved in oil. Thus, a free-radical generator that is an oxidation initiator for the active ingredients must be avoided. Indeed, various active ingredients, and in particular pheromones, consist of fatty chains having at least one unsaturation and they should be protected from oxidation. The use of a free-radical polymerization agent leads to oxidation and degradation of these sensitive compounds. Moreover, the polymerization process described in WO2012095444 can in no case lead to a core-shell structure because polymerization occurs via the free-radical generator that diffuses from the outside toward the core of the particle and thus creates a polymerization gradient but not a core-shell structure.

Furthermore, the microparticles of the prior art do not make it possible to encapsulate certain active ingredients.

Thus, there arises from the prior art a need for a process for producing particles containing an active ingredient, in particular an oxidation-sensitive active ingredient, more particularly a pheromone; which is a gentle process that makes it possible to protect said pheromone from oxidation and degradation and the gradual and passive release thereof without external intervention.

DESCRIPTION OF THE INVENTION

Background Definitions:

Alkali-swellable emulsions (ASE) are copolymers of (meth)acrylic acid and alkyl acrylate produced by free-radical emulsion polymerization which have the property when neutralized by a base such as sodium hydroxide or ammonia to become water-soluble and to modify the rheology of water.

Hydrophobically modified alkali-swellable emulsions (HASE) are copolymers obtained like ASE but whose composition further comprises hydrophobic macromonomers having the general formula:

(I)

Where m is an integer generally greater than 5 and where R is a hydrophobic carbon group. They also have the capacity to modify the rheology of the aqueous solution.

The object of the invention consists in solving the problems of the products and processes of the prior art by using rheology modifiers such as copolymers of (meth)acrylic acid and alkyl acrylate to produce particles that are stable in suspension and capable of releasing semiochemical substances, in particular pheromones, more particularly lepidopteran pheromones, more particularly fatty-chain pheromones, and even more particularly lepidopteran fatty-chain pheromones.

To that end we found that, surprisingly, it was possible to produce particles having the advantages of those obtained by coacervation (particles with a solid shell that prevents their destabilization) and the advantages of the use of mixtures of wax(es) and oil(s) to obtain low-cost, biodegradable systems composed of natural substances. The distinctive feature of the invention lies in the use of molecules that, under certain pH conditions, play the part of surfactant and, under other pH conditions, harden and become the solid shells of particles.

The advantage of such a process is that it is simple to implement and the particle size is easily adjustable, which has an effect on the release kinetics of pheromone.

Moreover, the particles according to the invention protect the active ingredient from oxidation, particularly when it is a pheromone, and allow controlled release of said active ingredient contained in the particles, more particularly when the active ingredient is a pheromone. Indeed, in the case of the present invention, and unlike the techniques of the prior art, encapsulation is carried out with no chemical agent, with no chemical reaction other than a gentle change of the pH of the formulation, which only induces a spatial rearrangement of the copolymer used. The active ingredient is not altered by the process, protected once the particle is formed, and is then gradually released into the environment as shown in the examples below.

It is thus a first object of the invention to provide particles comprising a solid shell surrounding a core, characterized in that:
  the solid shell comprises at least one polymer, preferably an acrylic copolymer,
  the core comprises a mixture of wax, oil and pheromone,
  the core represents 90-99% by weight of the particles.

In a particular embodiment, the acrylic copolymer of the solid shell of the particles according to the invention is selected from copolymers of (meth)acrylic acid and alkyl acrylate.

It may be a matter of alkali-swellable emulsion (ASE)-type copolymers as defined above.

In another embodiment, the acrylic copolymer may be selected from hydrophobically modified alkali-swellable emulsions (HASE) as defined above.

The HASE-type acrylic copolymers going into the composition of the particles of the present invention derive from copolymerization of the monomers described above. They may be prepared according to the methods described in WO 2011/104599, WO 2011/104600 and EP1778797.

Polymers other than acrylic copolymers may be envisaged from the moment when they exhibit rheology modifier-type behavior, namely when they play the part of surfactant in mixture with the fatty phase and can be flocculated by a chemical agent or by modifying the pH of the medium, for example.

In an embodiment of the invention, the acrylic copolymer has carboxylate functions that are neutralized at a rate between 50% and 100%, preferably between 65% and 100% and more preferably between 75% and 100%.

Preferably, the acrylic copolymer is a HASE-type copolymer and is characterized in that it contains:
Between 30% and 40% by weight of methacrylic acid,
Between 45% and 60% by weight of ethyl acrylate,
Between 5% and 20% by weight of a macromonomer having the general formula (I):

(I)

Where m is an integer between 1 and 40, preferably between 10 and 30, and where R is a hydrophobic carbon group having the general formula $C_nH_{2n+1}$ wherein n is an integer between 9 and 25, preferably between 10 and 20, and more preferably is equal to 12.

In a particular embodiment, the particles according to the present invention have a core composed of
10% to 90% by weight of wax, particularly from 60% to 80% by weight of wax,
10% to 90% by weight of oil, particularly 8% to 35% by weight of oil,
0.1% to 25% by weight of pheromone, particularly from 0.5% to 20% by weight of pheromone,
0 to 0.8% by weight, particularly from 0.1% to 0.5% by weight of stabilizer.

In the description of the present invention, the expression "particles" refers to particles having an average size varying from 0.2 μm to a few tens of microns, such as 0.5 to 100 μm, or from 1 to 70 μm, or 1 to 40 μm. When the particles are spherical, the average particle size is the average particle diameter. When the particles are non-spherical, i.e., they have a longer dimension and a shorter dimension, the average particle size is the size of the longest dimension of the particles. Particle size may be measured according to methods well-known to a person skilled in the art, such as by laser particle-size analysis.

By "wax" is meant, in the context of the invention, a lipophilic compound that is solid at room temperature (around 25° C.) and atmospheric pressure (760 mmHg). The waxes that may be used in a composition according to the invention may be selected from waxes of animal, vegetable, mineral origin or synthetic waxes and mixtures thereof. One may in particular use hydrocarbon waxes such as beeswax, lanolin wax and Chinese insect waxes; rice wax, carnauba wax, candelilla wax, jojoba wax, ouricury wax, esparto wax, cork fiber wax, sugar cane wax, Japanese wax and sumac wax, montan wax, microcrystalline waxes, paraffins and ozocerite; polyethylene waxes, waxes obtained by Fischer-Tropsch synthesis and waxy copolymers and esters thereof. Mention may also be made of waxes obtained by catalytic hydrogenation of animal or vegetable oils having linear or branched $C_8$-$C_{32}$ fatty chains. Among those, particular mention may be made of hydrogenated jojoba oil, hydrogenated sunflower oil, hydrogenated castor oil, hydrogenated copra oil and hydrogenated lanolin oil, di-(trimethylol-1,1,1-propane) tetrastearate. One may also use waxes obtained by transesterification and hydrogenation of vegetable oils, such as castor oil or olive oil, such as waxes sold under the names Phytowax ricin 16L64® and 22L73® and Phytowax Olive 18L57 by the company SOPHIM.

By "oil" is meant a water-immiscible nonaqueous compound that is liquid at room temperature (around 25° C.) and atmospheric pressure (760 mmHg). The oil according to the invention may be selected from vegetable oils. In a particular manner, the oil according to the invention will be selected from the group consisting of sunflower oil, peanut oil, soybean oil, rapeseed oil, corn oil, olive oil, grape oil, walnut oil, linseed oil, palm oil, coconut oil, argan oil, avocado oil, almond oil, hazel nut oil, pistachio oil, rice oil, cotton seed oil, wheat germ oil, sesame oil, or mixtures thereof. Preferably, the oil is selected as a function of the crop one wishes to protect from insect pests, in particular lepidopterans.

A stabilizer, or a mixture of stabilizer, may be contained in the core of the particles according to the invention. The stabilizer may be selected from the group consisting of n-butyl-4-hydroxybenzoate (BHB), tocopherol, ter-butyl-hydroquinone (TBH), n-propyl-gallate (PG), t-butyl-hydroxyanisole (BHA), methyl para-hydroxybenzoate (MHB), N,N diethyl-toluamide (DT), t-butyl-hydroxy-toluene (BHT) and α-thioglycerin (TG), nitroxides and alkoxyamines and mixtures thereof. The one or more stabilizers protect the core of the particles of the invention from oxidation.

The solid-polymer-shell particles of the present invention may be in the form of more or less spherical structures capable of adapting to or of adhering at least in part to the surfaces that receive them (for example fabric, paperboard, plastic).

The solid-polymer-shell particles of the present invention may be in aqueous suspension form or they may be in the form of solid particles that are more or less flexible or rigid as a function of the needs of the application.

It is also an object of the present invention to provide an aqueous suspension of particles according to the invention characterized in that it contains between 1% and 70% by weight, particularly between 5% and 60% by weight of particles according to the invention. The pH of a suspension according to the invention is between 2 and 7, more particularly between 4 and 7.

The one or more pheromones contained in the particles according to the invention are particularly insect pheromones, more particularly fatty-chain insect pheromones. More particularly, it is a matter of lepidopteran fatty-chain pheromones. In a particular manner, the particles according to the invention contain lepidopteran sex pheromones.

The sex pheromones of insects like lepidopterans are characterized in that they are composed of mixtures of molecules having unsaturated alcohol-, ester- or aldehyde-terminated fatty chains.

Lepidopterans are four-winged insects covered with a scaly dust and having a coiled proboscis, which undergo complete metamorphosis and whose grubs are called caterpillars and nymphs chrysalides.

As pheromone contained in the particles according to the invention, mention may be made of pheromones of *Tuta absoluta, Plodia interpunctella, Plutella xylostella, Gortyna xanthenes, Agrotis* spp., for example. More particularly, the pheromone may be a sex pheromone of the European grapevine moth, *Lobesia botrana*, a lepidopteran grapevine pest.

The adjustment of the wax/oil/pheromone ratios depends on the solubility of the pheromones in the oil/wax mixture.

A fourth object of the invention is an aqueous suspension of particles according to the invention characterized in that it contains between 1% and 70% by weight of particles, particularly between 5% and 60% by weight of particles, more particularly between 10% and 50% by weight, even more particularly between 20% and 50% by weight, and has a pH between 2 and 7, preferably between 4 and 7.

A fifth object of the invention is the process for preparing a suspension of particles according to the invention comprising the following steps:
 a) Prepare a fatty phase comprising oil, wax and pheromone, and optionally one or more stabilizers,
 b) Heat the fatty phase to a temperature above the melting point of the wax,
 c) Prepare an aqueous solution comprising the acrylic polymer, having a pH between 7.5 and 10 and heated to a temperature similar to that of the fatty phase,
 d) Mix the fatty phase in the aqueous solution to form a dispersion of fatty-phase droplets in a continuous aqueous phase,
 e) Acidify at a pH between 2 and 7, preferably between 4 and 7, in order to solidify the acrylic polymer.

In a particular embodiment of the process, the pH of the aqueous solution is adjusted by means of an alkaline solution such as sodium hydroxide, potassium hydroxide, sodium carbonate or ammonia solution.

In a particular embodiment, the fatty phase is heated to a temperature between 50° C. and 80° C., above the melting point of the wax.

In a particular embodiment, the acidification of the mixture according to step e) may be carried out with the help of an acid solution such as hydrochloric acid, phosphoric acid, sulfuric acid, until a pH between 2 and 7, preferably between 4 and 7, is reached, which makes it possible to obtain the fluid suspension of the invention.

In a particular embodiment of the process according to the invention, the particles according to the invention may be collected via an additional liquid/solid separation step such as centrifugation, for example.

A sixth object of the invention is the use of particles or a suspension according to the invention to spray foliage.

A seventh object of the invention is directed to a device for applying a composition containing one of the particles according to the invention, said device being of syringe type comprising a barrel and a plunger, said barrel being open at one end to allow the plunger to slide and being provided with an opening at the other end that allows the composition to pass and blocks the plunger. Such a device may advantageously be a syringe preloaded with a composition containing particles according to the invention. Such a device is particularly well suited for depositing a dose of particles in or on the surface of a substrate. Such a device thus avoids handling of the composition by the operator's hands or fingers, which thus avoids contamination of the composition.

An eighth object of the invention is the use of the particles or aqueous suspension according to the invention to lure lepidopterans according to a trapping protocol or a sexual confusion protocol. Preferably, the crops protected by the particles are grapevine, field crops (rice, corn, cotton, soy, sunflower, for example), market garden crops (tomatoes, lettuce, sweet peppers, melons, cucumbers, cabbage or spinach, for example), and ornamental trees or fruit trees (apple trees, peach trees, pear trees, citrus trees, for example), and forests (such as pine or oak forests, for example), or shrubs (such as boxwood, for example).

In another embodiment, the present invention is also directed to a process for protecting an agricultural plot, in particular a cultivated agricultural plot, against lepidopterans comprising applying a composition comprising particles according to the invention.

In a particular embodiment, the agricultural plot may be a covered plot such as a greenhouse or a nursery or an open plot such as a field or a forest.

The application may be carried out by spraying or depositing a suspension according to the invention, for example.

EXAMPLES

Materials:
 The pheromones are either purchased from industrial producers or produced by M2i Development according to known processes. In the case of the products synthesized by M2i, their characterizations are validated by a comparative analysis with a reference sample by gas chromatography.

The acrylic rheology modifiers are HASE-type acrylic copolymers provided by the company Coatex. They are prepared according to methods known to a person skilled in the art by means of a mercaptan-type chain-transfer agent.

The HASE 1 copolymer used for the following exemplifications consists of:
 35.5% by weight of methacrylic acid,
 52.4% by weight of ethyl acrylate,
 12% by weight of a macromonomer having the formula (I) wherein m=30 and n=12.

Pheromone release is measured in a 30° C. ventilated oven according to two methods, either by measuring the weight loss of the samples placed in the oven or by measuring the residual concentration of the pheromone in the sample by gas chromatography, according to the following methodology.

Release Measurement Methodology:
 Principle
 A release curve is determined for each pheromone in order to be able to evaluate changes in the pheromone concentrations in the samples by comparison with an internal standard sample.

Experimental Methods

Place 3 g of formulated product spread in a thin film in a container (Petri dish). Repeat the operation several times. Place the Petri dishes in an oven at the selected temperature, 30° C. in the examples below. At a time n, remove a Petri dish from the oven and then analyze the pheromone residue in the sample.

Preparation of Analytical Samples

Sample at T=0: Liquid-liquid extraction of latex with HCl and MeCy

Sample at T=0+n: Idem

At a time n, remove a Petri dish from the oven and dissolve its contents with HCl (1N) and make up 20 ml. Transfer to a 50 ml graduated flask, rinse with 10 ml of HCl (1N). Add 20 ml of hexane and extract.

General Protocol for Producing Pheromone-containing Microparticles:

Components of the Formulation:

| Aqueous phase: | HASE rheology modifier |
| | $H_2O$ |
| | 10% NaOH |
| Solution 1 | Wax/oil |
| | Pheromone |
| Solution 2 | $H_3PO_4$ (4%) |

Procedure:

Solution 1 is prepared by melting the wax and the pheromone in a double-jacketed reactor provided with mechanical stirring (IKA) and with a standard anchor- or impeller-type stirrer shaft. The reactor's internal temperature must be above the melting point of the wax.

In a second double-jacketed reactor, provided with mechanical stirring (IKA) and with a standard anchor- or impeller-type stirrer shaft, under stirring, the aqueous phase is prepared by loading the water, the sodium hydroxide and the rheology additive. This mixture is heated to a temperature above the melting point of the wax.

When solution 1 is melted, it is added dropwise to the aqueous phase over roughly 5 min.

Solution 2 is then added dropwise over 15 min. The mixture is stirred for 5 min before being cooled and returned to room temperature.

The suspension of microparticles is then drained from the reactor.

Example 1

Preparation of Vine Moth (*Eupoecilia Ambiguella*) Pheromone Capsules

The preparation of vine moth pheromone capsules was carried out according to the general procedure above with the amounts of reagents presented below. These tests show that the pheromone content in the capsules can be modified as needed.

| Test | 1 | 2 | 3 |
|---|---|---|---|
| Beeswax/Sunflower oil ratio | 10/30 | 10/30 | 10/30 |
| Pheromone content | 2% | 1% | 0.5% |

-continued

| Test | 1 | 2 | 3 |
|---|---|---|---|
| Pheromone | 1.5 g | 0.75 g | 0.375 g |
| HASE 1 | 3.75 g | 3.75 g | 3.75 g |
| $H_2O$ | 30.95 g | 30.95 g | 30.95 g |
| NaOH (10%) | 1.45 g | 1.45 g | 1.45 g |
| Beeswax | 7.875 g | 7.875 g | 7.875 g |
| Sunflower oil | 22.91 g | 23.66 g | 24.04 g |
| $H_3PO_4$ (4%) | 3.22 g | 3.22 g | 3.22 g |

Likewise, the ratios between the components of the matrix, beeswax and sunflower oil in our examples can be modified in order to adjust the viscosity of the matrix contained in the capsules.

| Test | 1 | 4 | 5 | 6 |
|---|---|---|---|---|
| Beeswax/Sunflower oil ratio | 10/30 | 20/30 | 10/40 | 0/100 |
| Pheromone content | 2% | 2% | 2% | 2% |
| Pheromone | 1.5 g | 1.5 g | 1.5 g | 1.5 g |
| HASE 1 | 3.75 g | 3.75 g | 3.75 g | 3.75 g |
| $H_2O$ | 30.95 g | 30.95 g | 30.95 g | 30.95 g |
| NaOH (10%) | 1.45 g | 1.45 g | 1.45 g | 1.45 g |
| Beeswax | 7.875 g | 12.912 g | 6.456 g | 0 g |
| Sunflower oil | 22.91 g | 17.87 g | 24.324 g | 30.78 g |
| $H_3PO_4$ (4%) | 3.22 g | 3.22 g | 3.22 g | 3.22 g |

Example 2

Figure 1:
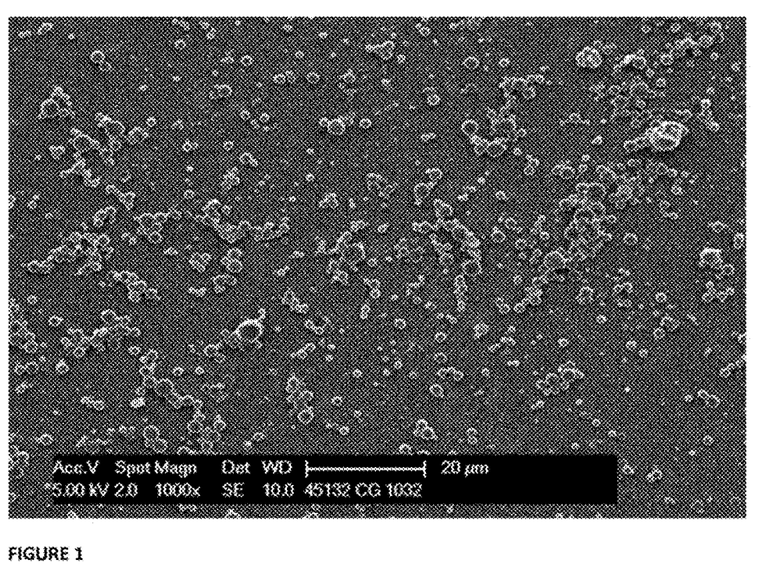
FIG. 1, FIG. 2 and FIG. 3 represent photographs obtained with a scanning electron microscope and are an illustration of the dimensions of the particles obtained: a few microns in this example.
Figure 2:
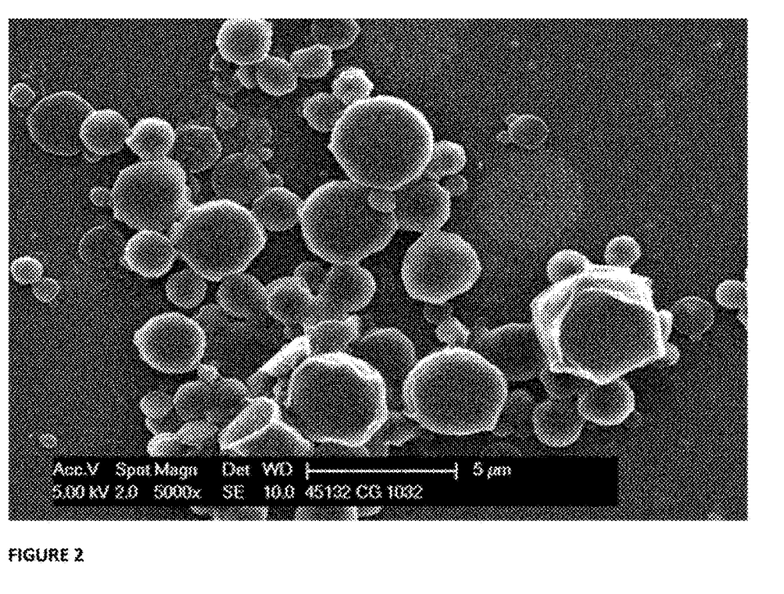
Figure 3:
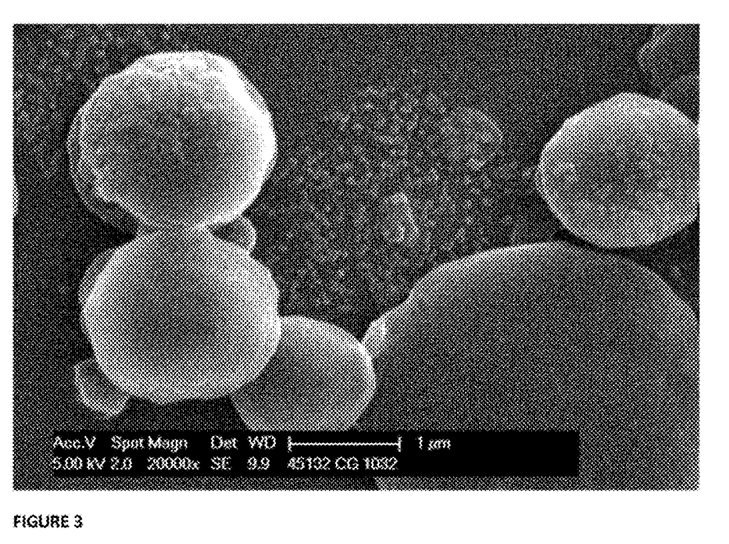

Preparation of European Grapevine Moth (*Lobesia Botrana*) Pheromone Capsules

The preparation of European grapevine moth pheromone capsules was carried out according to the general procedure above with the amounts of reagents presented in the following table.

| Components of the formulation | | Test 7 |
|---|---|---|
| Aqueous phase | HASE 1 | 3.7 g |
| | $H_2O$ | 30.9 g |
| | NaOH (10%) | 1.4 g |
| Solution 1 | Beeswax | 7.8 g |
| | Sunflower oil | 22.9 g |
| | Pheromone | 1.5 g |
| Solution 2 | $H_3PO4$ (4%) | 3.2 g |

Example 3

Preparation of a Vaporizable Suspension of European Grapevine Moth Pheromone Capsules To a suspension of 2 g of capsules containing the European grapevine moth pheromone, derived from example 2, is added 30 g of water. The fluid preparation is placed in a bottle provided with a manual sprayer. This particle suspension can be vaporized in fine droplets and thus form a thin film.

Example 4

Release Kinetics

The release kinetics of the vine moth pheromone capsule preparation tests 1, 2 and 3 described in example 1 are presented below.

|  | Residual pheromone content (mg) | | |
| --- | --- | --- | --- |
| Time (days) | Test 1 | Test 2 | Test 3 |
| 0 | 62.8 | 31.4 | 15.7 |
| 3 | 42.0 | 24.6 | 14.9 |
| 7 |  |  | 13.9 |
| 10 | 30.3 | 19.4 |  |
| 14 | 26.4 | 17.4 | 12.1 |
| 17 |  | 15.6 | 12.9 |
| 21 | 22.2 | 9.8 | 9.9 |
| 24 | 22.4 |  | 8.5 |
|  | Test 1 | Test 2 | Test 3 |
| Average daily release rate (mg) | 1.75 | 0.9 | 0.28 |

These examples show that the capsules produced in example 1 make it possible to release the pheromone over long periods with a daily rate controlled by the ratio of the pheromone to the mass of the capsule.

Likewise, the pheromone release of the capsules derived from tests 4, 5 and 6 was carried out in a controlled manner with daily rates between 0.5 and 2 mg/day of pheromone.

Example 5

Preparation of a Suspension of Mediterranean Corn Borer Pheromone Particles

The preparation of a suspension of Mediterranean corn borer pheromone was carried out according to the general procedure above with the amounts of reagents presented below.

| Components of the formulation | | Test 8 | Test 9 | Test 10 |
| --- | --- | --- | --- | --- |
| Aqueous phase | HASE 1 | 3.7 g | 6.63 | 132.74 |
|  | H₂O | 30.9 g | 27.9 | 558.58 |
|  | NaOH (10%) | 1.4 g | 2.56 | 51.32 |
| Solution 1 | Beeswax | 7.8 g | 13.9 | 278.94 |
|  | Sunflower oil | 22.9 g | 33.2 | 664.07 |
|  | Pheromone | 1.5 g | 10 | 200 |
| Solution 2 | H₃PO4 (4%) | 3.2 g | 5.7 | 113.98 |
| Suspension total mass | | 56.5 | 100 | 2000 |

Example 6

Coating of Particles Obtained in Example 5 and Release of the Pheromone

The suspension of particles 10 was deposited on paperboard pads.

The table below represents the residual amounts of the two compounds, (11Z)-hexadecenyl acetate/(11Z)-hexadecenol (9:1), of the pheromonal mixture in the particle coating over time.

| Time (days) | MAJORITY COMPOUND Amount of pheromone | MINORITY COMPOUND Amount of pheromone |
| --- | --- | --- |
| 0 | 360.0 | 40.0 |
| 3 | 297.1 | 36.2 |
| 8 | 312.5 | 38.1 |
| 13 | 335.3 | 35.9 |
| 20 | 316.2 | 37.9 |
| 24 | 319.2 | 38.0 |
| 34 | 323.0 | 38.9 |
| 38 | 290.1 | 34.7 |
| 45 | 245.0 | 29.2 |

These data correspond to an average daily rate of the majority component of 1.6 mg/day and of the minority component of 0.15 mg/day, and show that beyond 45 days, the release of the two compounds is still effective. Moreover, it should be noted that the ratio of the two compounds present remains virtually constant during the study.

Example 7

Preparation of Pine Processionary Moth Pheromone Capsules

The preparation of a suspension of pine processionary moth pheromone was carried out according to the general procedure above with the amounts of reagents presented below.

| Components of the formulation | | Example 1 |
| --- | --- | --- |
| Aqueous phase | HASE 1 | 0.94 g |
|  | H₂O | 7.74 g |
|  | NaOH (10%) | 0.36 g |
| Solution 1 | Beeswax | 1.92 g |
|  | Sunflower oil | 5.62 g |
|  | Pheromone | 0.23 g |

The table below represents the residual amount of pheromone in the particle matrix over time.

| Duration (days) | Amount of residual pheromone (mg) |
| --- | --- |
| 1 | 13.6 |
| 11 | 13.6 |
| 14 | 13.3 |
| 18 | 13.3 |
| 30 | 13.1 |

This study shows that with a 3% load of processionary pheromone, the release rate is slow and makes it possible to propose forest treatment systems that are active for 9 months.

Example 8

Deposition of a Capsule Suspension by Means of a Plastic Syringe

Capsules containing pine processionary pheromone were packaged into syringes. Each syringe contains an amount of pheromone that can be deposited on a substrate in a processionary caterpillar trap. This provides a simple model for depositing pheromone in a trap.

The invention claimed is:

1. Particles comprising a solid shell surrounding a core, wherein:
the solid shell comprises at least one acrylic copolymer,
the core comprises a mixture of wax, oil and pheromone,
the core represents 90-99% by weight of the particles,
wherein the acrylic copolymer of the solid shell is selected from HASE-type copolymers and wherein it contains:
between 30% and 40% by weight of methacrylic acid,
between 45% and 60% by weight of ethyl acrylate,
between 5% and 20% by weight of a macromonomer having the general formula (I):

(I)

where m is an integer between 1 and 40, and where R is a hydrophobic carbon group having the general formula $C_nH_{2n+1}$ wherein n is an integer between 9 and 25.

2. The particles according to claim 1, wherein the acrylic copolymer has carboxylate functions that are neutralized at a rate between 50% and 100%.

3. The particles according to claim 1 wherein the core contains:
10% to 90% by weight of wax,
10% to 90% by weight of oil,
0.1% to 25% by weight of pheromone,
0 to 0.8% by weight, of stabilizer.

4. The particles according to claim 1 wherein the wax is selected from the group consisting of beeswax, lanolin wax and Chinese insect waxes; rice wax, carnauba wax, candelilla wax, jojoba wax, ouricury wax, esparto wax, cork fiber wax, sugar cane wax, Japanese wax and sumac wax, montan wax, microcrystalline waxes and mixtures thereof.

5. The particles according to claim 1 where in the oil according to the invention is selected from the group consisting of sunflower oil, peanut oil, soybean oil, rapeseed oil, corn oil, olive oil, grape oil, walnut oil, linseed oil, palm oil, coconut oil, argan oil, avocado oil, almond oil, hazel nut oil, pistachio oil, rice oil, cotton seed oil, wheat germ oil, sesame oil and mixtures thereof.

6. The particles according to claim 3, wherein the stabilizer is selected from the group consisting of n-butyl-4-hydroxybenzoate (BHB), tocopherol, ter-butyl-hydroquinone (TBH), n-propyl-gallate (PG), t-butyl-hydroxyanisole (BHA), methyl para-hydroxybenzoate (MIHB), N,N-diethyl-toluamide (DT), t-butyl-hydroxy-toluene (BHT) and α-thioglycerin (TG), nitroxides and alkoxyamines and mixtures thereof.

7. The particles according to claim 1, wherein the pheromone is selected from lepidopteran sex pheromones.

8. An aqueous suspension of particles according to claim 1 wherein the suspension contains between 1% and 70% by weight of particles, and has a pH between 2 and 7.

9. A process for preparing a suspension of particles according to claim 8 comprising the following steps:
a) Prepare a fatty phase comprising oil, wax and pheromone, and optionally one or more stabilizers,
b) Heat the fatty phase to a temperature above the melting point of the wax,
c) Prepare an aqueous solution comprising the acrylic polymer, having a pH between 7.5 and 10 and heated to a temperature similar to that of the fatty phase,
d) Mix the fatty phase in the aqueous solution to form a dispersion of fatty-phase droplets in a continuous aqueous phase,
e) Acidify at a pH between 2 and 7, in order to solidity the acrylic polymer.

10. Method for spraying foliage comprising the application of particles according to claim 1 onto foliage in need thereof.

11. Method for luring lepidopterans according to a trapping protocol or a sexual confusion protocol in crops such as grapevine, field crops, garden market crops, fruit trees or ornamental trees comprising applying particles according to claim 1 into said crops in need thereof.

12. A process for protecting an agricultural plot, in particular a cultivated agricultural plot, against lepidopterans comprising applying a composition comprising particles according to claim 1.

* * * * *